(12) United States Patent
Chang et al.

(10) Patent No.: US 10,582,898 B2
(45) Date of Patent: Mar. 10, 2020

(54) TOMOGRAPHY SYSTEM AND METHOD THEREOF

(71) Applicant: Institute of Nuclear Energy Research, Atomic Energy Council, Executive Yuan, R.O.C, Taoyuan (TW)

(72) Inventors: Chia-Hao Chang, Taoyuan (TW); Shu-Chun Chang, Taoyuan (TW); Fan-Pin Tseng, Taoyuan (TW); Yu-Ching Ni, Taoyuan (TW)

(73) Assignee: INSTITUTE OF NUCLEAR ENERGY RESEARCH, ATOMIC ENERGY COUNCIL, EXECUTIVE YUAN, R.O.C., Taoyuan (TW)

( * ) Notice: Subject to any disclaimer, the term of this patent is extended or adjusted under 35 U.S.C. 154(b) by 117 days.

(21) Appl. No.: 15/924,729

(22) Filed: Mar. 19, 2018

(65) Prior Publication Data

US 2019/0117172 A1 Apr. 25, 2019

(30) Foreign Application Priority Data

Oct. 24, 2017 (TW) .............................. 106136555 A

(51) Int. Cl.
*A61B 6/03* (2006.01)
*A61B 6/00* (2006.01)
*G06T 11/00* (2006.01)
*G01V 5/00* (2006.01)
*H04N 5/357* (2011.01)
*G01N 23/087* (2018.01)

(52) U.S. Cl.
CPC ............... *A61B 6/032* (2013.01); *A61B 6/03* (2013.01); *A61B 6/4241* (2013.01); *A61B 6/482* (2013.01); *A61B 6/5205* (2013.01); *A61B 6/5235* (2013.01); *G01V 5/005* (2013.01); *G01V 5/0041* (2013.01); *G06T 11/005* (2013.01); *A61B 6/585* (2013.01); *G01N 23/087* (2013.01); *G01N 2223/206* (2013.01); *G01N 2223/419* (2013.01); *G01N 2223/423* (2013.01); *G06T 2207/10081* (2013.01); *G06T 2211/408* (2013.01); *H04N 5/357* (2013.01)

(58) Field of Classification Search
CPC ....................................................... A61B 6/482
See application file for complete search history.

(56) References Cited

U.S. PATENT DOCUMENTS 10,121,267 B2 * 11/2018 Lin .................. G06T 11/008
2004/0102688 A1 * 5/2004 Walker ................ A61B 6/032
600/407

* cited by examiner

*Primary Examiner* — Kenneth J Malkowski
(74) *Attorney, Agent, or Firm* — Locke Lord LLP; Tim Tingkang Xia, Esq.

(57) ABSTRACT

A tomography method includes: a step of having a photon counting detector to undergo a relative motion with respect to an X-Ray source, and capturing 2×N projected energy spectral data at 2×N individual discrete projection angles that divide the relative motion, the N being a positive integer; a step of reforming the 2×N projected energy spectral data at the 2×N individual discrete projection angles and establishing corresponding projection intensity data; and, a step of basing on the projection intensity data and the 2×N projected energy spectral data at the 2×N individual discrete projection angles to calculate the material decomposition images. In addition, a tomography system is also provided.

12 Claims, 5 Drawing Sheets

TOMOGRAPHY SYSTEM AND METHOD THEREOF

CROSS REFERENCE TO RELATED APPLICATION

This application claims the benefit of Taiwan Patent Application Serial No. 106136555, filed on Oct. 24, 2017, the subject matter of which is incorporated herein by reference.

BACKGROUND OF THE INVENTION

(1) Field of the Invention

The invention relates to a tomography system and a tomography method, and more particularly to a tomography system and a method of the tomography system that can increase the number of energy window of a photon counting detector-based multi-energy computed tomography.

(2) Description of the Prior Art

Generally, an image-detecting system of a typical X-Ray computed tomography (CT) usually apply a conventional energy integrating detector (EID). However, such a detector can only obtain X-Ray attenuation information after penetrating mass. As the development of a dual-energy computed tomography system, the energy-related information of a penetrating X-Ray can then be obtained.

Recently, in comparison with the dual-energy CT technology, a new photon counting detector (PCD) based technology is introduced to apply a photon counting detector to provide more detailed energy-related information. In the marketplace, most of the commercial photon counting detectors are within the dual-energy scope. The multi-energy (more than two energy levels) photon counting detectors are few and expensive. Generally speaking, the more energy levels the photon counting detector has, the more complicate the signal-processing circuit is. Namely, more comparators units are required, and thus more costly and advanced technology would be involved. Thereupon, the dead time of the detector would be increased inevitably by having signals to pass complicated circuits, and therefrom the photon flux received by the detector, as well as the applications thereof, would be substantially limited.

SUMMARY OF THE INVENTION

The present invention provides a tomography system and a method thereof by basing on a photon counting detector having two tomographic energy levels. In a circumstance of maintaining the same level of data acquisition time and image spatial resolution, an object of having more energy windows (with the number of energy window larger than 3) computed tomography can be achieved by implementing the tomography at discrete projection angles and the image-processing technique.

In the present invention, the tomography method includes: a step of having a photon counting detector to undergo a relative motion with respect to an X-Ray source, and capturing 2×N projected energy spectral data at 2×N individual discrete projection angles that divide the relative motion, the N being a positive integer; a step of reforming the 2×N projected energy spectral data at the 2×N individual discrete projection angles and establishing corresponding projection intensity data; and, a step of basing on the projection intensity data and the 2×N projected energy spectral data at the 2×N individual discrete projection angles to calculate the material the material decomposition images.

In one embodiment of the present invention, the step of "reforming the 2×N projected energy spectral data at the 2×N individual discrete projection angles" includes a step of defining a low-energy threshold and a high-energy threshold larger than the low-energy threshold, each of the 2×N projected energy spectral data at the 2×N individual discrete projection angles being divided by the high-energy threshold and the low-energy threshold so as to produce correspondingly a high-energy spectral data and a low-energy spectral data, a mean energy of the high-energy spectral data being larger than that of the low-energy spectral data.

In one embodiment of the present invention, the step of "establishing corresponding projection intensity data" includes: a step of forming 2×N full-energy projected energy spectral data at the 2×N individual discrete projection angles by combining the individual high-energy spectral data of the 2×N projected energy spectral data at the 2×N individual discrete projection angles with the corresponding low-energy spectral data, a step of integrating the 2×N full-energy projected energy spectral data individually at the 2×N individual discrete projection angles so as to obtain corresponding intensity data at the 2×N discrete projection angles, and a step of combining the intensity data at the 2×N discrete projection angles so as to form the projection intensity data.

In one embodiment of the present invention, the step of "capturing 2×N projected energy spectral data at 2×N individual discrete projection angles" includes: a step of separating the 2×N projected energy spectral data at the 2×N individual discrete projection angles into a group of odd-numbered energy spectral data and a group of even-numbered energy spectral data; and, a step of setting an odd-numbered high-energy threshold to the group of odd-numbered energy spectral data and an even-numbered high-energy threshold to the group of even-numbered energy spectral data, the odd-numbered high-energy threshold being different to the even-numbered high-energy threshold.

In one embodiment of the present invention, the step of "setting an odd-numbered high-energy threshold to the group of odd-numbered energy spectral data and an even-numbered high-energy threshold to the group of even-numbered energy spectral data" includes a step of setting an odd-numbered low-energy threshold to the group of odd-numbered energy spectral data and an even-numbered low-energy threshold to the group of even-numbered energy spectral data, the odd-numbered high-energy threshold being larger than the odd-numbered low-energy threshold, the even-numbered high-energy threshold being larger than the even-numbered low-energy threshold.

In one embodiment of the present invention, after the step of "capturing 2×N projected energy spectral data at 2×N individual discrete projection angles", a step is further included to transform analog signals of the 2×N projected energy spectral data at the 2×N individual discrete projection angles into corresponding digital signals.

In one embodiment of the present invention, after the step of "capturing 2×N projected energy spectral data at 2×N individual discrete projection angles", a step is further included to correct the 2×N projected energy spectral data at the 2×N individual discrete projection angles.

In one embodiment of the present invention, the step of "having a photon counting detector to undergo a relative motion with respect to an X-Ray source" includes: a step of having the X-Ray source to generate an energy spectrum to penetrate through an object to be tested; and, a step of having the photon counting detector to detect the energy spectrum so as to obtain correspondingly the projected energy spectral data.

In the present invention, the tomography system includes an X-Ray source, a photon counting detector, a rebinning unit and a reconstruction unit. The photon counting detector, located oppositely to the X-Ray source so as to undergo a relative motion with respect to the X-Ray source, is to capture 2×N projected energy spectral data at 2×N individual discrete projection angles that divide the relative motion, in which the N is a positive integer. The rebinning unit, coupling the photon counting detector, is to reform the 2×N projected energy spectral data at the 2×N individual discrete projection angles and to establish corresponding projection intensity data. The reconstruction unit, coupling the rebinning unit, is to base on the projection intensity data and the 2×N projected energy spectral data at the 2×N individual discrete projection angles to calculate the material decomposition images.

In one embodiment of the present invention, the photon counting detector has two energy windows, each of the 2×N projected energy spectral data at the 2×N individual discrete projection angles having correspondingly a high-energy spectral data and a low-energy spectral data, a mean energy of the high-energy spectral data being larger than that of the low-energy spectral data.

In one embodiment of the present invention, the rebinning unit forms 2×N full-energy projected energy spectral data at the 2×N individual discrete projection angles by integrating the individual high-energy spectral data of the 2×N projected energy spectral data at the 2×N individual discrete projection angles with the corresponding low-energy spectral data, integrates the 2×N full-energy projected energy spectral data at the 2×N individual discrete projection angles so as to obtain intensity data at the 2×N discrete projection angles, and combines the intensity data at the 2×N discrete projection angles so as to form the full-angles projection intensity data.

In one embodiment of the present invention, the 2×N projected energy spectral data at the 2×N individual discrete projection angles is separated into a group of odd-numbered energy spectral data and a group of even-numbered energy spectral data, an odd-numbered high-energy threshold and an odd-numbered low-energy threshold are set to the group of odd-numbered energy spectral data, the odd-numbered high-energy threshold is larger than the odd-numbered low-energy threshold, an even-numbered high-energy threshold and an even-numbered low-energy threshold are set to the group of even-numbered energy spectral data, the even-numbered high-energy threshold is larger than the even-numbered low-energy threshold, and the odd-numbered high-energy threshold is different to the even-numbered high-energy threshold.

In one embodiment of the present invention, the tomography system further includes a preprocessing unit coupled with the reconstruction unit, and the preprocessing unit is to correct the 2×N projected energy spectral data at the 2×N individual discrete projection angles.

In one embodiment of the present invention, the tomography system further includes a data acquisition unit. The data acquisition unit, coupling the photon counting detector, is to transform analog signals of the 2×N projected energy spectral data at the 2×N individual discrete projection angles into corresponding digital signals.

In one embodiment of the present invention, the tomography system further includes a motion control unit connecting the X-Ray source and the photon counting detector. The motion control unit is to have the photon counting detector to undergo the relative motion with respect to the X-Ray source, the X-Ray source generates an energy spectrum to penetrating through an object to be tested, and the photon counting detector detects the energy spectrum so as to obtain correspondingly the projected energy spectral data.

As stated above, the tomography system and the tomography method provided by the present invention is provided by basing on a photon counting detector having two energy windows. By presenting different energy thresholds for capturing two groups of projected energy spectral data at N respective discrete projection angles, thus the tomographic time can be shortened, and the radiation dose of the object can be reduced. By sampling the two groups of projected energy spectral data at N respective discrete projection angles, the number of energy windows can be increased to be larger than 2, such that the accuracy of the material decomposition of the object to be tested can be improved, or the number of material analyzed from the object to be tested can be increased.

Furthermore, in the present invention, the projection intensity data are calculated to compensate possible aliasing produced by the two groups of projected energy spectral data at N respective discrete projection angles. Hence, by providing the present invention, the number of energy windows can be increased without sacrificing the image spatial resolution and the acquisition time.

In addition, by providing the present invention, since no expensive multi-energy (with the number of energy windows larger than 3) photon counting detector is needed anymore for increasing the number of energy windows, so the entire hardware cost of the system can be substantially reduced.

All these objects are achieved by the tomography system and the method of the tomography system described below.

BRIEF DESCRIPTION OF THE DRAWINGS

The present invention will now be specified with reference to its preferred embodiment illustrated in the drawings, in which.

DESCRIPTION OF THE PREFERRED EMBODIMENT

The invention disclosed herein is directed to a tomography system and a method of the tomography system. In the following description, numerous details are set forth in order to provide a thorough understanding of the present invention. It will be appreciated by one skilled in the art that variations of these specific details are possible while still achieving the results of the present invention. In other instance, well-known components are not described in detail in order not to unnecessarily obscure the present invention.

Figure 1:
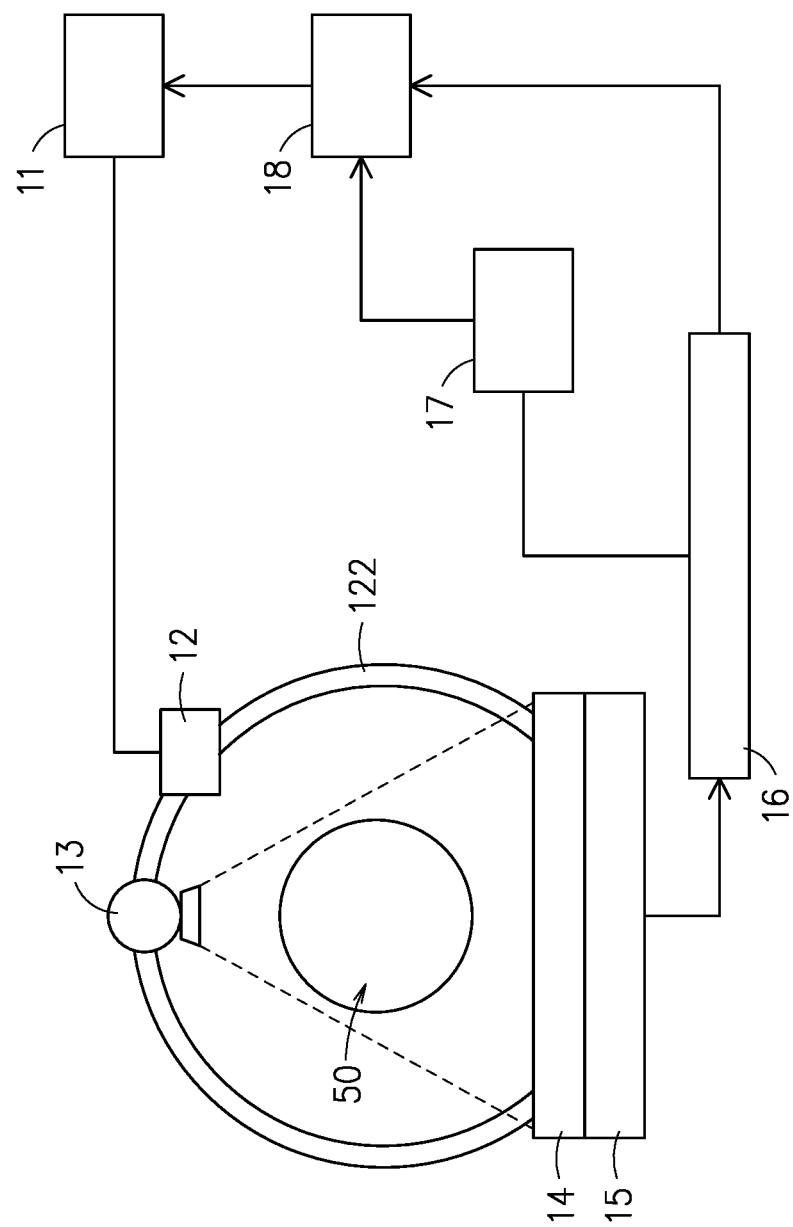
FIG. 1 is a schematic view of an embodiment of the tomography system in accordance with the present invention.

Referring now to FIG. 1, a schematic view of an embodiment of the tomography system in accordance with the present invention is schematically shown. The tomography system 10, adopting a three-generation CT framework, applies a photon counting detector (PCD) 14 to replace the energy integrating detector (EID). In this embodiment, the computed tomography imaging system 10 includes an operation unit 11, a motion control unit 12, an X-Ray source 13, a photon counting detector (PCD) 14, a data acquisition unit (DAQ) 15, a data preprocessing unit 16, a data rebinning unit 17 and an image reconstruction unit 18.

In this embodiment, the operation unit 11 can include at least an input device, a memory device, a display device and a corresponding controller. The input device is provided for an operator to input parameters. The controller can base on the inputted parameters to execute specific steps upon related components of the tomography system 10. Then, the memory device is to store and provide, thereafter, corresponding data and/or images obtained from the aforesaid steps. The display device is to display images retrieved from the memory device for the operator to inspect.

In this embodiment, the operation unit 11 is connected with the motion control unit 12' and the motion control unit 12 is connected with the X-Ray source 13 and the photon counting detector 14. As shown in FIG. 1, the motion control unit 12 includes a rail 122 for the photon counting detector 14 and the X-Ray source 13 to be arranged thereon, and an object to be tested 50 is disposed between the photon counting detector 14 and the X-Ray source 13. After the operator inputs the parameters to the input device of the operation unit 11, the input device of the operation unit 11 would forward these parameters to the controller, and then the controller of the operation unit 11 would issue corresponding motion signals to the motion control unit 12. Thus, the motion control unit 12 can drive the photon counting detector 14 and the X-Ray source 13 to undergo corresponding motions. At the same time, the X-Ray source 13 would generate an energy spectrum to penetrate the object to be tested 50, and thereby the photon counting detector 14 can detect a corresponding energy spectrum, so that a respective projected energy spectral data can be obtained. Based on such an arrangement, a group of projected energy spectral data in discrete projection angles can be obtained by dividing the motions of the photon counting detector 14 with respect to the X-Ray source 13 at a predetermined angular interval. It is preferably assumed that each said group has N or 2×N discrete projection angles, where the N is a positive integer. It shall be explained that, in this embodiment, different energy thresholds are preset to further divide each of the projected energy spectral data into different projected energy spectral data in discrete projection angles.

Figure 2:
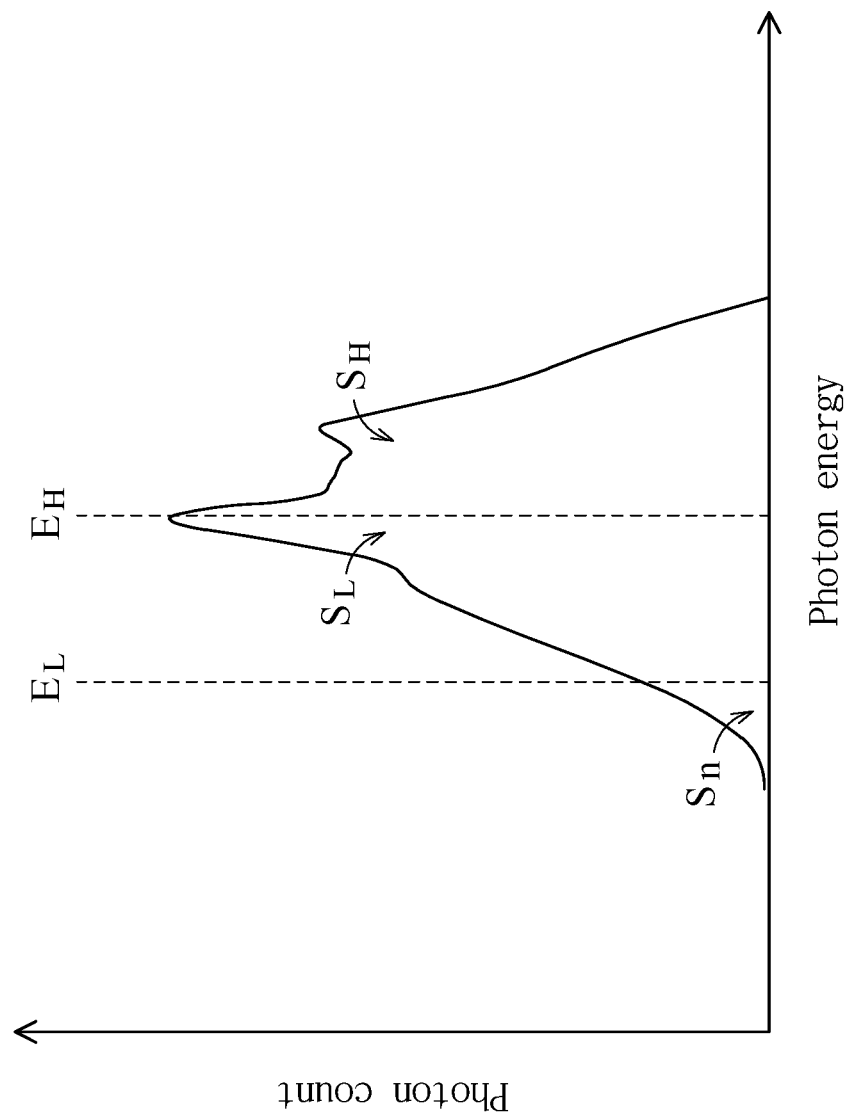
FIG. 2 is a schematic plot showing a relationship between the photon counting detector and the energy thresholds in accordance with the present invention.

Referring now to FIG. 2, a schematic plot showing a relationship between the photon counting detector and the energy thresholds in accordance with the present invention is provided. In this example of FIG. 2, a specific discrete angle is selected to present the projected energy spectral data. In FIG. 2, the horizontal axis stands for the photon energy, while the vertical axis thereof stands for the photon count. The photon counting detector is assumed to have two energy windows, i.e. a high-energy threshold $E_H$ and a low-energy threshold $E_L$. Any photon energy below the low-energy threshold $E_L$ is treated as an electronic noise Sn and thus be filtered out. Any photon energy between the low-energy threshold $E_L$ and the high-energy threshold $E_H$ is assorted into a low-energy spectral data $S_L$, and any photon energy higher than the high-energy threshold $E_H$ is assorted into a high-energy spectral data $S_H$. Definitely, a mean photon energy of the high-energy spectral data $S_H$ is larger than that of the low-energy spectral data $S_L$. In addition, a full-energy image is consisted of all the photon energies in the high-energy spectral data $S_H$ and the low-energy spectral data $S_L$. In addition, corresponding intensity data for the high-energy spectral data $S_H$ and the low-energy spectral data $S_L$ can be obtained individually by integrating photon energies in the high-energy spectral data $S_H$ and the low-energy spectral data $S_L$, respectively.

Referring back to FIG. 1, the data acquisition unit 15 is coupled with the photon counting detector 14 so as to transform each of the projected energy spectral data in an analog form into a corresponding digital signal. The data preprocessing unit 16 is coupled with the data acquisition unit 15 so as to receive the two groups of projected energy spectral data at N respective discrete projection angles from the data acquisition unit 15. The data preprocessing unit 16 corrects the two groups of projected energy spectral data at N respective discrete projection angles. In particular, the photon counting detector 14 would induce pulse pileup of signals due to an excessive event rate of incident photons, and thereby loss in photon count and/or incomplete collection of electric charges caused by some specific physical factors would bias the received energy spectral data. Hence, the data preprocessing unit 16 of this embodiment is particularly designed to perform correction and/or compensation upon imaging uniformity, pulse pile-up, charge sharing, charge trapping, K-escape X-ray and so on. In some other embodiments, the preprocessing unit 16 can receive directly the two groups of projected energy spectral data at N respective discrete projection angles, by bypassing the data acquisition unit 15, and then perform the necessary correction.

In this present invention, the data rebinning unit 17 is coupled with the photon counting detector 14 in an indirect manner. By having the embodiment of FIG. 1 as a typical example, the photon counting detector 14 is firstly connect with the data preprocessing unit 16, and then the data preprocessing unit 16 is connected to the rebinning unit 17. The preprocessing unit 16 is to transmit the two corrected groups of projected energy spectral data at N respective discrete projection angles to the data rebinning unit 17. Then, the data rebinning unit 17 reforms these two groups of projected energy spectral data at N respective discrete projection angles by integrating corresponding projection intensity data. In details, the data rebinning unit 17 produces two groups of full-energy spectral data at N respective discrete projection angles by including each of individual high-energy spectral data and the corresponding low-energy spectral data from the group of projected energy spectral data at N respective discrete projection angles. Then, the data rebinning unit integrates each of full-energy spectral data at N respective discrete projection angles so as to obtain corresponding intensity data, so as to obtain 2×N intensity data from the group of full-energy spectral data at N respective discrete projection angles. The data rebinning unit 17 finally combines these two groups of intensity data at N respective discrete projection angles into a unique group of full angle projection intensity data.

In this embodiment, the image reconstruction unit 18 is coupled with both the preprocessing unit 16 and the rebinning unit 17. The reconstruction unit 18 is to receive the two corrected groups of projected energy spectral data at N respective discrete projection angles from the preprocessing unit 16 and the unique group of full angle projection intensity data from the rebinning unit 17. According to the unique group of projection intensity data and the two corrected groups of projected energy spectral data at N respective discrete projection angles, an iterative reconstruction algorithm is applied to calculate the material decomposition images of the multi-energy (number of the energy window is at least larger than 3) material decomposition.

Upon the aforesaid arrangement, it is clear that the tomography system of the present invention is based on a two energy windows structure having the photon counting detector 14, and utilizes different preset energy thresholds to reform the group of projected energy spectral data captured at N respective discrete projection angles, such that the radiation dose of the object 50 can be reduced by shortening the acquisition time. Also, by providing the two groups of projected energy spectral data at N respective discrete projection angles, the number of energy windows can be increased to be a number larger than 2; such that the accuracy of the material decomposition of the object to be tested 50 can be improved, or the material number analyzed from the object to be tested 50 can be increased.

Furthermore, in this embodiment, the unique group of full angle projection intensity data is utilized to compensate possible aliasing caused by the two groups of projected energy spectral data at N respective discrete projection angles. Thus, by providing the present invention, the number of energy windows can be increased without sacrificing the image spatial resolution and the acquisition time.

In addition, in this embodiment of the present invention, since no expensive multi-energy (with the number of energy windows larger than 3) photon counting detector is needed anymore for increasing the number of energy windows, so the entire hardware cost of the system can be substantially reduced.

Figure 3:
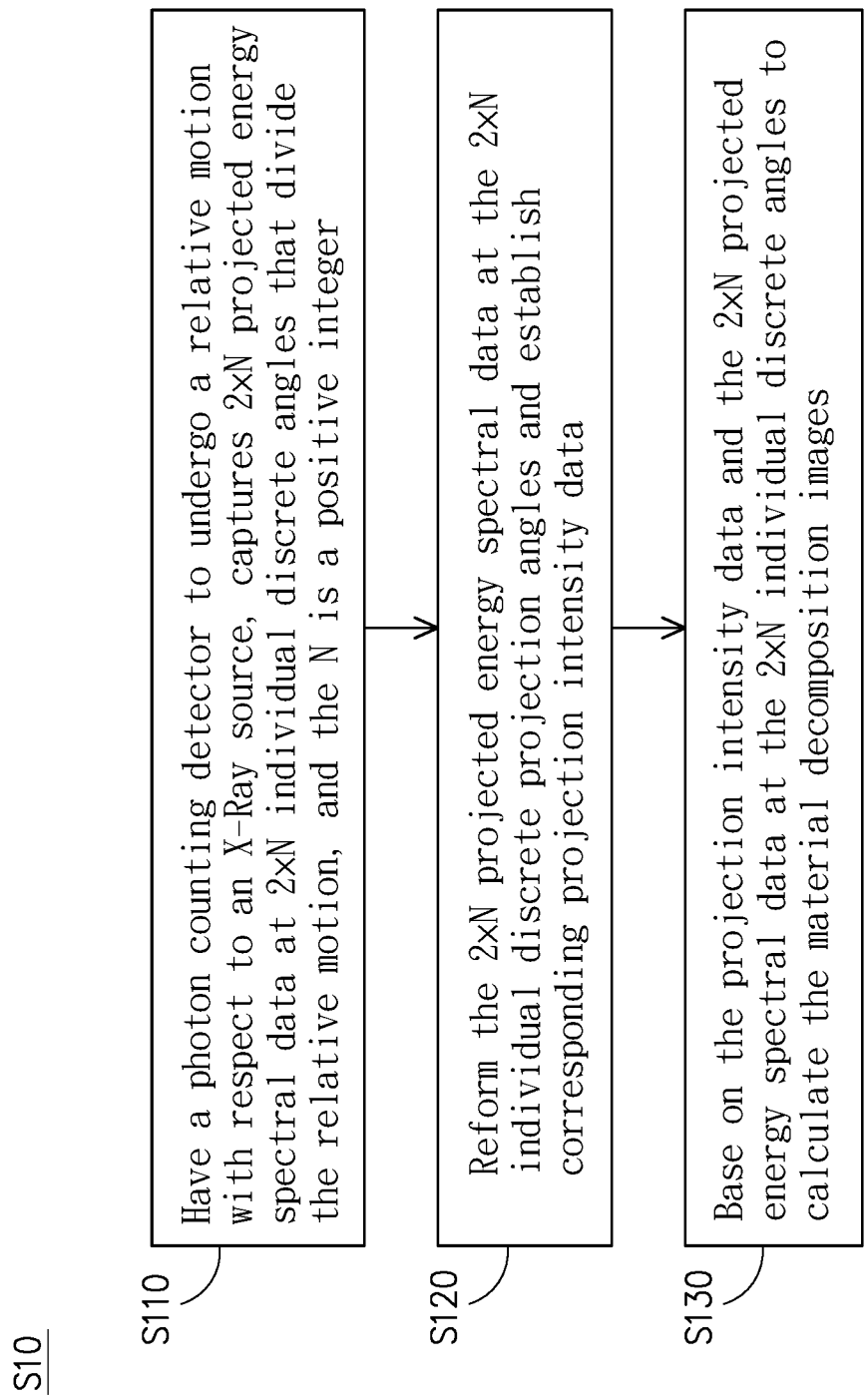
FIG. 3 is a flowchart of an embodiment of the tomography method in accordance with the present invention.

Referring now to FIG. 3, a flowchart of an embodiment of the tomography method in accordance with the present invention is shown. The tomography method S10 herein, applicable to the tomography system 10 of FIG. 1, includes Step S110 to Step S130.

In Step S110, a photon counting detector 14 and an X-Ray source 13 undergo a relative motion. The entire relative motion is divided into 2×N sections by a predetermined angular interval, in which N is a positive integer. In each section of the related motion, one projected energy spectral data is sampled, so that a total of 2×N projected energy spectral data at 2×N discrete projection angles can be obtained.

In details, the number of energy windows of the photon counting detector 14 applied in this embodiment is 2. After every angular interval, the X-Ray source 13 would generate an energy spectrum to penetrate through an object to be tested 50. By having the photon counting detector 14 to detect the energy spectrum, then totally 2×N corresponding projected energy spectral data at 2×N respective discrete projection angles can be obtained. These 2×N projected energy spectral data at 2×N respective discrete projection angles can be sorted into a group of odd-numbered energy spectral data and another group of even-numbered energy spectral data. Namely, in this embodiment, while in sampling these 2×N data at these 2×N discrete projection angles, the projected energy spectral data obtained from an odd-time sampling is attributed to the group of odd-numbered energy spectral data, while the projected energy spectral data obtained from an even-time sampling is attributed to the group of even-numbered energy spectral data.

For example, in the case that the angular interval is 1 degree, then, for a 360-degree motion, the 2×N would be 360 degrees/angular interval, i.e. N=180. Namely, in each group, a total of 180 discrete projection angles is determined by a 2-degree angular interval, and a projected energy spectral data is sampled at each discrete projection angle. The projected energy spectral data sampled at the 1st, 3rd, 5th, 7th, ... , 359th sampling, based on a sampling per 2 degree, are attributed to the group of odd-numbered energy spectral data, which the group of odd-numbered energy spectral data includes 180 projected energy spectral data. Similarly, the projected energy spectral data sampled at the 2nd, 4th, 6th, 7th, ... , 360th sampling are attributed to the group of even-numbered energy spectral data, which the group of even-numbered energy spectral data includes 180 projected energy spectral data.

Figure 4A:
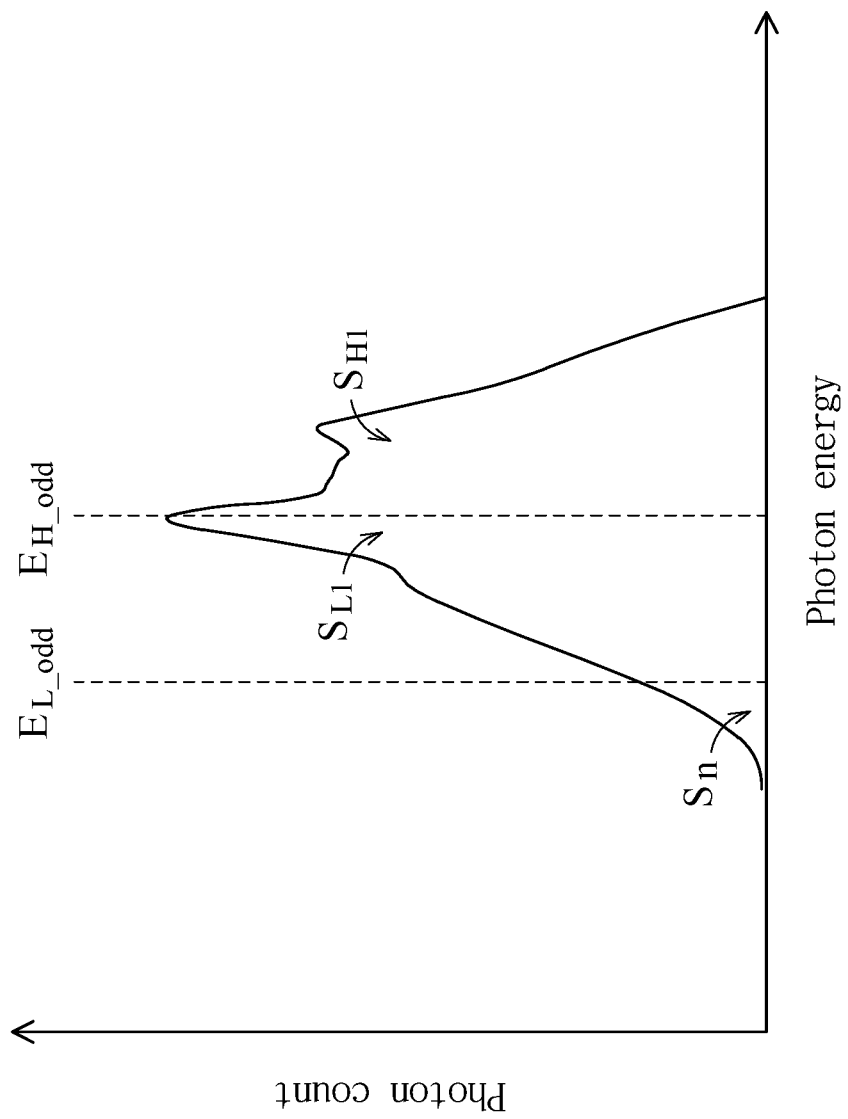
FIG. 4A is a schematic plot showing a typical odd-numbered energy spectral data in the group of odd-numbered energy spectral data in accordance with the present invention.
Figure 4B:
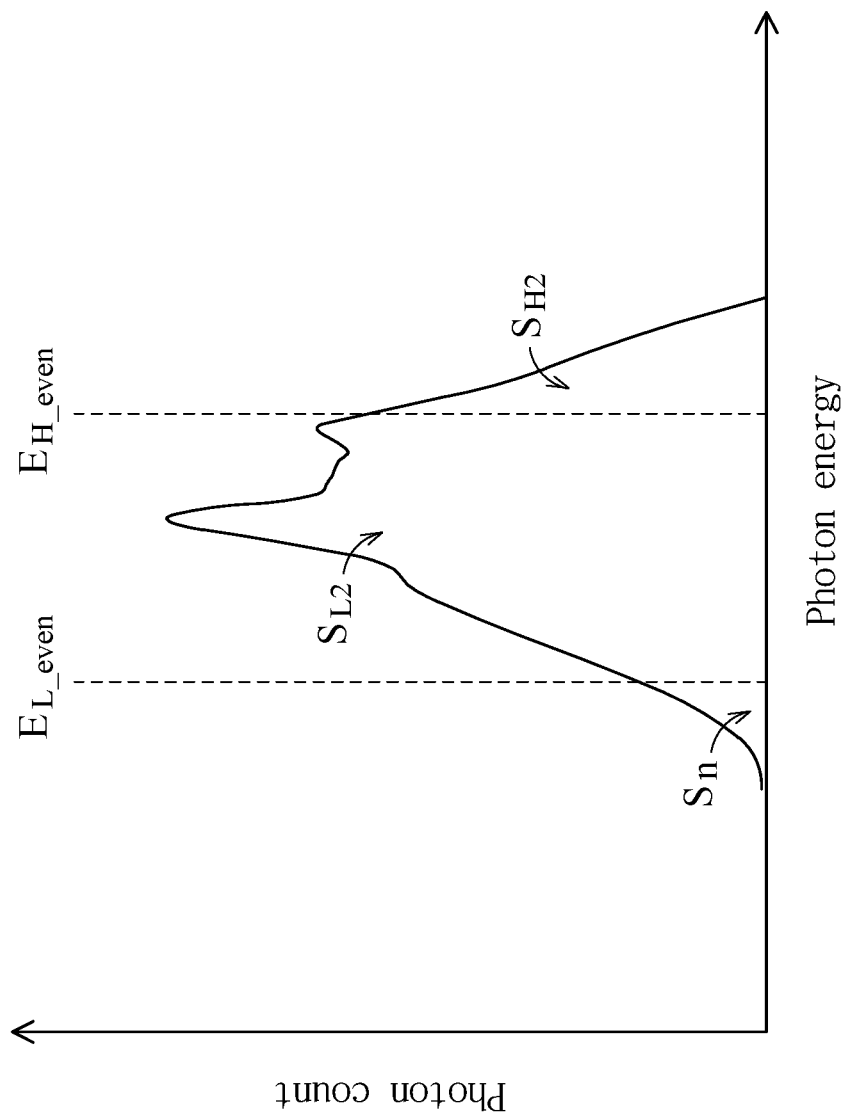
FIG. 4B is a schematic plot showing a typical even-numbered energy spectral data in the group of even-numbered energy spectral data in accordance with the present invention.

In this embodiment, each of the projected energy spectral data in the two groups of projected energy spectral data at N respective discrete projection angles can be further defined into a high-energy spectral data and a low-energy spectral data. By having the embodiment of the tomography method S10 as a typical exemplary example of the present invention, refer now to FIG. 4A and FIG. 4B; where FIG. 4A is a schematic plot showing a typical odd-numbered energy spectral data in the group of odd-numbered energy spectral data in accordance with the present invention, and FIG. 4B is a schematic plot showing a typical even-numbered energy spectral data in the group of even-numbered energy spectral data in accordance with the present invention. As shown in FIG. 4A, in a single odd-numbered energy spectral data, an odd-numbered high-energy threshold $E_{H\_odd}$ and an odd-numbered low-energy threshold $E_{L\_odd}$ are defined, in which the odd-numbered high-energy threshold $E_{H\_odd}$ is larger than the odd-numbered low-energy threshold $E_{L\_odd}$. Any photon energy below the odd-numbered low-energy threshold $E_{L\_odd}$ would be treated as an electronic noise Sn to be filtered out. Photon energies between the odd-numbered low-energy threshold $E_{L\_odd}$ and the odd-numbered high-energy threshold $E_{H\_odd}$ are used to form an odd-numbered low-energy spectral data $S_{L1}$, while any photon energy larger than the odd-numbered high-energy threshold $E_{H\_odd}$ is used to form an odd-numbered high-energy spectral data $S_{H1}$. As shown in FIG. 4B, in a single even-numbered energy spectral data, an even-numbered high-energy threshold $E_{H\_even}$ and an even-numbered low-energy threshold $E_{L\_even}$ are defined, in which the even-numbered high-energy threshold $E_{H\_even}$ is larger than the even-numbered low-energy threshold $E_{L\_even}$. Any photon energy below the even-numbered low-energy threshold $E_{L\_even}$ would be treated as the electronic noise Sn to be filtered out. Photon energies between the even-numbered low-energy threshold $E_{L\_even}$ and the even-numbered high-energy threshold $E_{H\_even}$ are used to form an even-numbered low-energy spectral data $S_{L2}$, while any photon energy larger than the even-numbered high-energy threshold $E_{H\_even}$ is used to form an even-numbered high-energy spectral data $S_{H2}$. In this embodiment, the odd-numbered high-energy threshold $E_{H\_odd}$ is different to the even-numbered high-energy threshold $E_{H\_even}$, but the odd-numbered low-energy threshold $E_{L\_odd}$ is equal to the even-numbered low-energy threshold $E_{L\_even}$. As shown in FIG. 4A and FIG. 4B, the even-numbered high-energy threshold $E_{H\_even}$ is greater than the odd-numbered high-energy threshold $E_{H\_odd}$. In this embodiment, sequential sampling is adopted to perform orderly the switching of the high-energy thresholds of the photon counting detector 14, so that all the corresponding projected energy spectral data for the two groups at N respective discrete projection angles can be obtained. Namely, the odd-numbered high-energy threshold $E_{H\_odd}$ and the odd-numbered low-energy threshold $E_{L\_odd}$ are adopted firstly to capture the odd-numbered high-energy spectral data $S_u$ and the odd-numbered high-energy spectral data $S_{H1}$, then the even-numbered high-energy threshold $E_{H\_even}$ and the even-numbered low-energy threshold $E_{L\_even}$ are adopted secondly to capture the even-numbered high-energy spectral data $S_{L2}$ and the even-numbered high-energy spectral data $S_{H2}$, then the odd-numbered high-energy threshold $E_{H\_odd}$ and the odd-numbered low-energy threshold $E_{L\_odd}$ are adopted thirdly to capture the odd-numbered high-energy spectral data $S_{L1}$ and the odd-numbered high-energy spectral data $S_{H1}$, and so on. Thereby, all the corresponding projected energy spectral data for the two groups at N respective discrete projection angles can be obtained orderly. In another embodiment, return-type sampling is adopted. In the sampling, the odd-numbered high-energy threshold $E_{H\_odd}$ and the odd-numbered low-energy threshold $E_{L\_odd}$ are firstly adopted to capture the group of odd-numbered energy spectral data clockwisely or counterclockwisely, and then the even-numbered high-energy threshold $E_{H\_even}$ and the even-numbered low-energy threshold $E_{L\_even}$ are secondly adopted to capture the group of even-numbered energy spectral data counterclockwisely or clockwisely (reverse to the aforesaid direction for capturing the group of odd-numbered energy spectral data), such that all the corresponding projected energy spectral data for the two groups at N respective discrete projection angles can be obtained.

In this embodiment, after all the corresponding projected energy spectral data for the two groups at N respective discrete projection angles are captured, following steps are performed. Firstly, each of the 2×N projected energy spectral data as an analog signal is transformed into a corresponding digital signal. Then, correction is carried out upon the 2×N projected energy spectral data. By having FIG. 1 for typical explanation, the data acquisition unit 15 transforms one analog signal of the 2×N projected energy spectral data into a corresponding digital signal, and transmits the 2×N projected energy spectral data to the preprocessing unit 16 for data correction. Since the pulse pileup of signals would be induced at the photon counting detector 14 due to an excessive event rate of incident photons, it is quite possible that loss in photon count and/or incomplete collection of electric charges caused by some specific physical factors would bias the received energy spectral data. Hence, in this embodiment, the data preprocessing unit 16 is introduced to perform correction and/or compensation upon imaging uniformity, pulse pile-up, charge sharing, charge trapping, K-escape X-ray and so on. In another embodiment, the data preprocessing unit 16 can receive and calibrate directly the 2×N projected energy spectral data.

Referring now to FIG. 3, after Step S110 has been performed, Step S120 is performed by reforming the 2×N projected energy spectral data and establishing corresponding projection intensity data. In details, the data rebinning unit 17 forms two groups of full-energy projected energy spectral data at N discrete projection angles by combining the N high-energy spectral data and the corresponding N low-energy spectral data into the 2×N projected energy spectral data. As shown in FIG. 4A, the odd-numbered high-energy spectral data $S_{L1}$ and the odd-numbered high-energy spectral data $S_{H1}$ are integrated to form a full-energy projected energy spectral data at a specific angle. As shown in FIG. 4B, the even-numbered low-energy spectral data $S_{L2}$ and the even-numbered low-energy spectral data $S_{H2}$ are combined to form another full-energy projected energy spectral data at a specific angle. The similar process is kept going till all two groups of full-energy projected energy spectral data at N respective discrete projection angles are obtained. Then, the data rebinning unit 17 integrates individually the 2×N full-energy projected energy spectral data to form correspondingly two groups of intensity data at N discrete projection angles. Namely, each of the 2×N full-energy projected energy spectral data is processed to obtain a corresponding intensity data. Then, the data rebinning unit 17 combines the 2×N intensity data to form a group of projection intensity data.

After the projection intensity data is obtained in Step S120, Step S130 is performed to base on the projection intensity data and the 2×N projected energy spectral data to calculate the material decomposition images. Referring to FIG. 1, the image reconstruction unit 18 receives the 2×N corrected projected energy spectral data from the data preprocessing unit 16 and the group of projection intensity data from the data rebinning unit 17. Based on these projection intensity data and the projected energy spectral data, the iterative image reconstruction algorithm is applied to calculate the material decomposition images of a multi-energy (number of energy windows at least larger than 3) material decomposition. The material decomposition image can be stored in the memory device of the operation unit 11 of FIG. 1, and can be displayed at the display device thereof for the operator to inspect.

For example, in this embodiment, the iterative image reconstruction algorithm is run by utilizing a minimized cost function. Variables for the cost function includes a system matrix, projected energy spectral data at N discrete projection angles, a group of projection intensity data, options of X-ray beam-hardening correction parameters and standardized parameters. The cost function can be expressed as follows:

$$\psi(c) = \sum_{jk} \frac{1}{\sigma_{jk}^2} [l_k(j) - l_k^{(M)}(j)]^2 + \quad (1)$$

$$\sum_{j} \frac{1}{\sigma_j^2} \left[ \sum_k L_k(j) \cdot \bar{\mu}_k - g_M(j) - g_M^{(BH)}(L) \right]^2 + wV(c);$$

$$l_k(j) = \sum_i \sum_{n=1}^N a_{jin} c_k(i); \text{ and} \quad (2)$$

$$L_k(j) = \sum_i a_{ji} c_k(i). \quad (3)$$

wherein the c in equation (1) is a vectorized material decomposition image, the $\psi(c)$ is the cost function of the decomposition image. A right-hand side of the equal sign of equation (1) includes the following three terms, (i)~(iii).

$$\sum_{jk} \frac{1}{\sigma_{jk}^2} [l_k(j) - l_k^{(M)}(j)]^2, \quad (i)$$

the energy spectral data term, in which the j is a number of projection X-ray photon beam, the k is a number of the decomposition materials, the $l_k(j)$ is a length of the decomposition material k along the photon beam j calculated by the reverse projection, the $l_k^{(M)}(j)$ is a length of the decomposition material k along the photon beam j after the material decomposition, the $\sigma_{jk}^2$ as a variance of $l_k^{(M)}(j)$ is a weighting factor for normalizing the energy spectral data, the $l_k(j)$ is calculated according to equation (2), the $a_{jin}$ is a system matrix factor, the i is a number of the imaging pixel, the n is a number of the energy spectral data at the n-th discrete angle (n=1, ..., N), and the $c_k(i)$ is the decomposition image of material k at a pixel number of i.

$$\sum_j \frac{1}{\sigma_j^2} \Big[\sum_k L_k(j) \cdot \bar{\mu}_k - g_M(j) - g_M^{(BH)}(L)\Big]^2, \quad\text{(ii)}$$

the intensity data term, in which the $L_k(j)$ is a length of the decomposition material k along the photon beam j after the material decomposition, the $\bar{\mu}_k$ is a mean linear attenuation coefficient of material k, the $g_M(j)$ is a projection intensity value along the photon beam j, the $g_M^{(BH)}(L)$ is a X-ray bean-hardening correction term at a length L, the $\sigma_j^2$ as a variance of $g_M(j)$ is a weighting factor of the normalizing intensity data term, the $L_k(j)$ is calculated according to equation (3), and the $a_{ji}$ is a system matrix factor of intensity data obtained from reconstructing the energy spectral data. (iii) wV(c) a term of normalization, in which the V(c) is a standardized term, and the w is a weighting factor for the normalized term.

Then, the iterative image reconstruction algorithm is applied to minimize the cost function including the aforesaid terms as as to obtain an optimal decomposition image $c_k(i)$ of each material k that fulfills the cost function, $$c_k(i) = c_k^{(0)}(i) - \frac{\frac{\partial \psi(c^{(0)})}{\partial c_k(i)}}{\sum_{ik} \frac{\partial^2 \psi(c^{(0)})}{\partial c_k(i) \partial c_k(i)}}. \quad (4)$$

In this equation (4), the $c_k^{(0)}(i)$ is an initial decomposition image of material k, the $c_{k'}(i')$ is an image of material k' at a pixel position i', the k' is not equal to the k, and the i' is not equal to the i.

In summary, the tomography system and the tomography method provided by the present invention is provided by basing on a photon counting detector having two energy windows. By presenting different energy thresholds to define two groups of projected energy spectral data at N respective discrete projection angles, thus the data acquisition time can be shortened, and radiation dose of the object can be reduced. By sampling the two groups of projected energy spectral data at N respective discrete projection angles, the number of energy windows can be increased to be larger than 2, such that the accuracy of the material decomposition of the object to be tested can be improved, or the number of material analyzed from the object to be tested can be increased.

Furthermore, in the present invention, the projection intensity data are calculated to compensate possible aliasing produced by the two groups of projected energy spectral data at N respective discrete projection angles. Hence, by providing the present invention, the number of energy windows can be increased without sacrificing the image spatial resolution and the acquisition time.

In addition, by providing the present invention, since no expensive multi-energy (with the number of energy windows larger than 3) photon counting detector is needed anymore for increasing the number of energy windows, so the entire hardware cost of the system can be substantially reduced.

While the present invention has been particularly shown and described with reference to a preferred embodiment, it will be understood by those skilled in the art that various changes in form and detail may be without departing from the spirit and scope of the present invention.

The invention claimed is:

1. A tomography method, comprising the steps of:
    having a photon counting detector to undergo a relative motion with respect to an X-Ray source, and capturing 2×N projected energy spectral data at 2×N individual discrete projection angles that divide the relative motion, the N being a positive integer;
    reforming the 2×N projected energy spectral data at the 2×N individual discrete projection angles, and establishing corresponding projection intensity data; and
    basing on the projection intensity data and the 2×N projected energy spectral data at the 2×N individual discrete projection angles to calculate the material decomposition images;
    wherein the step of reforming the 2×N projected energy spectral data at the 2×N individual discrete projection angles includes a step of defining a low-energy threshold and a high-energy threshold larger than the low-energy threshold, each of the 2×N projected energy spectral data at the 2×N individual discrete projection angles being divided by the high-energy threshold and the low-energy threshold so as to produce correspondingly a high-energy spectral data and a low-energy spectral data, a mean energy of the high-energy spectral data being larger than that of the low-energy spectral data; and
    wherein the step of establishing corresponding projection intensity value includes the steps of:
        forming 2×N full-energy projected energy spectral data at the 2×N individual discrete projection angles by combining the individual high-energy spectral data of the 2×N projected energy spectral data at the 2×N individual discrete projection angles with the corresponding low-energy spectral data;
        integrating the 2×N full-energy projected energy spectral data individually at the 2×N individual discrete projection angles so as to obtain corresponding intensity data at the 2×N discrete projection angles; and
        combining the intensity data at the 2×N discrete projection angles so as to form the projection intensity data.

2. The tomography method of claim 1, wherein the step of capturing 2×N projected energy spectral data at 2×N individual discrete projection angles includes the steps of:
    separating the 2×N projected energy spectral data at the 2×N individual discrete projection angles into a group of odd-numbered energy spectral data and a group of even-numbered energy spectral data; and
    setting an odd-numbered high-energy threshold to the group of odd-numbered energy spectral data and an even-numbered high-energy threshold to the group of even-numbered energy spectral data, the odd-numbered high-energy threshold being different to the even-numbered high-energy threshold.

3. The tomography method of claim 2, wherein the step of setting an odd-numbered high-energy threshold to the group of odd-numbered energy spectral data and an even-numbered high-energy threshold to the group of even-numbered energy spectral data includes a step of setting an odd-numbered low-energy threshold to the group of odd-numbered energy spectral data and an even-numbered low-energy threshold to the group of even-numbered energy spectral data, the odd-numbered high-energy threshold being larger than the odd-numbered low-energy threshold, the even-numbered high-energy threshold being larger than the even-numbered low-energy threshold.

4. The tomography method of claim 1, after the step of capturing 2×N projected energy spectral data at 2×N individual discrete projection angles, further including a step of transforming each of the 2×N projected energy spectral data at the 2×N individual discrete projection angles from analog signals into corresponding digital signals.

5. The tomography method of claim 1, after the step of capturing 2×N projected energy spectral data at 2×N individual discrete projection angles, further including a step of correcting the 2×N projected energy spectral data at the 2×N individual discrete projection angles.

6. The tomography method of claim 1, wherein the step of having a photon counting detector to undergo a relative motion with respect to an X-Ray source includes the steps of:
having the X-Ray source to generate an energy spectrum to penetrate through an object to be tested; and
having the photon counting detector to detect the energy spectrum so as to obtain correspondingly the projected energy spectral data.

7. A tomography system, comprising:
an X-Ray source;
a photon counting detector, located oppositely to the X-Ray source so as to undergo a relative motion with respect to the X-Ray source, capturing 2×N projected energy spectral data at 2×N individual discrete projection angles that divide the relative motion, the N being a positive integer;
a data rebinning unit, coupling the photon counting detector, being to reform the 2×N projected energy spectral data at the 2×N individual discrete projection angles and to establish corresponding projection intensity data; and
an image reconstruction unit, coupling the data rebinning unit, being to base on the projection intensity data and the 2×N projected energy spectral data at the 2×N individual discrete projection angles to calculate the material decomposition images;
wherein the step of reforming the 2×N projected energy spectral data at the 2×N individual discrete projection angles includes a step of defining a low-energy threshold and a high-energy threshold larger than the low-energy threshold, each of the 2×N projected energy spectral data at the 2×N individual discrete projection angles being divided by the high-energy threshold and the low-energy threshold so as to produce correspondingly a high-energy spectral data and a low-energy spectral data, a mean energy of the high-energy spectral data being larger than that of the low-energy spectral data; and
wherein the data rebinning unit forms 2×N full-energy projected energy spectral data at the 2×N individual discrete projection angles by combining the individual high-energy spectral data of the 2×N projected energy spectral data at the 2×N individual discrete projection angles with the corresponding low-energy spectral data, integrates each of the 2×N full-energy projected energy spectral data at the 2×N individual discrete projection angles so as to obtain corresponding intensity data at the 2×N discrete projection angles, and combines the intensity data at the 2×N discrete projection angles so as to form the full angle projection intensity data.

8. The tomography system of claim 7, wherein the photon counting detector has two energy windows, each of the 2×N projected energy spectral data at the 2×N individual discrete projection angles having correspondingly a high-energy spectral data and a low-energy spectral data, a mean energy of the high-energy spectral data being larger than that of the low-energy spectral data.

9. The tomography system of claim 7, wherein the 2×N projected energy spectral data at the 2×N individual discrete projection angles is separated into a group of odd-numbered energy spectral data and a group of even-numbered energy spectral data, an odd-numbered high-energy threshold and an odd-numbered low-energy threshold are set to the group of odd-numbered energy spectral data, the odd-numbered high-energy threshold is larger than the odd-numbered low-energy threshold, an even-numbered high-energy threshold and an even-numbered low-energy threshold are set to the group of even-numbered energy spectral data, the even-numbered high-energy threshold is larger than the even-numbered low-energy threshold, and the odd-numbered high-energy threshold is different to the even-numbered high-energy threshold.

10. The tomography system of claim 7, further including a data preprocessing unit coupled with the image reconstruction unit, the data preprocessing unit being to correct the 2×N projected energy spectral data at the 2×N individual discrete projection angles.

11. The tomography system of claim 7, further including a data acquisition unit coupled with the photon counting detector, the data acquisition unit being to transform analog signals of the 2×N projected energy spectral data at the 2×N individual discrete projection angles into corresponding digital signals.

12. The tomography system of claim 7, further including a motion control unit connecting the X-Ray source and the photon counting detector, the motion control unit being to have the photon counting detector to undergo the relative motion with respect to the X-Ray source, the X-Ray source generating an energy spectrum to penetrating through an object to be tested, the photon counting detector detecting the energy spectrum so as to obtain correspondingly the projected energy spectral data.

* * * * *